US00PP17079P2

(12) United States Plant Patent
Lemon

(10) Patent No.: US PP17,079 P2
(45) Date of Patent: Sep. 5, 2006

(54) ***GERANIUM* PLANT NAMED 'PATRIOT BRIGHT VIOLET'**

(50) Latin Name: *Pelargonium×hortorum*
Varietal Denomination: Patriot Bright Violet

(75) Inventor: David G. Lemon, Lompoc, CA (US)

(73) Assignee: Oglevee, Ltd., Connellsville, PA (US)

( * ) Notice: Subject to any disclaimer, the term of this patent is extended or adjusted under 35 U.S.C. 154(b) by 0 days.

(21) Appl. No.: 11/177,056

(22) Filed: Jul. 8, 2005

(51) Int. Cl.
*A01H 5/00* (2006.01)

(52) U.S. Cl. ..... Plt./329
(58) Field of Classification Search ..... Plt./329
See application file for complete search history.

*Primary Examiner*—Kent Bell
(74) *Attorney, Agent, or Firm*—The Webb Law Firm

(57) ABSTRACT

'Patriot Bright Violet' is a new variety of *geranium* that exhibits free flowering, good outdoor performance, and deep violet-red flowers with fluorescent orange eyes atop of mounding medium-dark green foliage.

1 Drawing Sheet

Botanical classification: *Pelargonium×hortorum.*
Varietal denomination: 'Patriot Bright Violet'.

BACKGROUND OF THE INVENTION

The present invention comprises a new and distinct cultivar of *Pelargonium×hortorum* known by the varietal name 'Patriot Bright Violet'. The new variety was discovered in Lompoc, Calif. The new variety is a result of cross breeding Pink Seedling #6421 (female parent) (unpatented) and 'Americana New Violet' (male parent). The purpose of the breeding program was to introduce a *geranium* having free branching. The new variety is similar in plant type to its female parent, but is dissimilar in flower color. The new variety is similar in flower color and earliness to its male parent, but exhibits more basal branching. The excellent greenhouse and good outdoor performance and free flowering nature of 'Patriot Bright Violet' distinguishes the new variety from other varieties known to the breeder. The new variety was first asexually reproduced by cuttings in Connellsville, Pa. The new variety has been trial and field tested and has been found to retain its distinctive characteristics and remain true to type through successive propagations.

The new variety was grown in a glass greenhouse in a 4" pot in Connellsville, Pa. using full light, 16° C. night temperature, 20° C. day temperature, and grown in a soilless media with constant fertilizer at 200–250 ppm nitrogen and potassium. The new variety exhibits developed roots at 21 days at an average temperature of 23° C. and has a response time of seven weeks from a rooted cutting to flowering in a 10 cm. container.

DESCRIPTION OF THE DRAWING

The accompanying photographic drawing illustrates the new variety, with the color being as nearly true as is possible with color illustrations of this type.

DESCRIPTION OF THE PLANT

Figure 1:
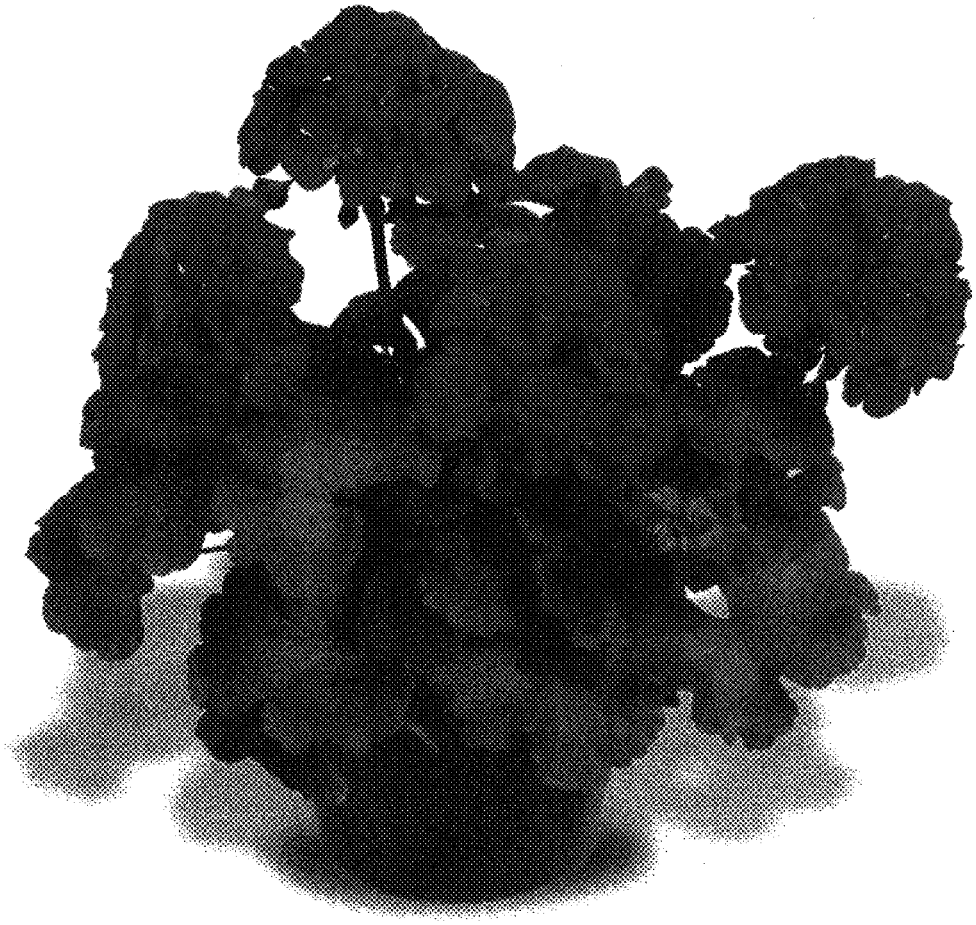

The following detailed description sets forth the characteristics of the new cultivar. The data which defines these characteristics were collected by asexual reproductions carried out in Connellsville, Pa. The color readings were taken indoors under 200–220 foot candles of cool white fluorescent light. The new variety was eight weeks from a rooted cutting when described. Color references are primarily to the 1966 R.H.S. Colour Chart of The Royal Horticultural Society of London.

PLANT

Market class: Zonal.
Time to initiate roots: Approximately 7–10 days at about 23° C.
Time to develop roots: Approximately 21 days at about 23° C.
Time to produce a finished flowering plant from a rooted cutting: About 7 weeks in a 10 cm. container.
Rooting habit: Good, normal.
Form: Round-mounded.
Height from media surface to top of foliage: 13.0–13.5 cm.
Height from media surface to top of flowers: 26.5–27.0 cm.
Plant diameter: 20.5–28.0 cm.
Strength: No artificial support is needed.
Branching habit: Free branching.
Stem:
- *Main stem length.*—8.5–9.5 cm.
- *Diameter.*—0.7–1.2 cm.
- *Color.*—Yellow-Green Group 144A.
- *Texture.*—Leathery texture.
- *Pubescence.*—Slight.
- *Internode length.*—1.4–1.5 cm.

Lateral branches:
- *Length.*—Primary: 3.8–7.0 cm. Secondary: 1.5 cm.
- *Diameter.*—Primary: 2.0 cm. Secondary: 0.8 cm.
- *Internode length.*—1.0–1.8 cm.
- *Texture.*—Leathery.
- *Pubescence.*—Slight.
- *Color.*—Yellow-Green Group 144B.

Foliage:
- *Arrangement.*—Alternate.
- *Stipules.*—Size: 0.45–1.1 cm. Color: Yellow-Green Group 144A.
- *Zone.*—Location: Very faint zone from outer edge of leaf to ½ of the way toward the center. Color: Green Group 137A.

*Size of leaf.*—Length: 5.2–6.1 cm. Width: 8.2–10.0 cm.
*Shape of leaf (generally).*—Reniform with a stalked base.
*Shape of apex.*—Rounded in accordance with reniform leaf shape.
*Shape of base.*—Cordate.
*Texture.*—Rough velvet.
*Aspect.*—Leaves have a very slight slope increasing from point of connection toward the margin.
*Margin type.*—Crenate.
*Pubescence.*—Upper surface: Moderate. Lower surface: Moderate.
*Color.*—Young leaves: Upper surface: Green Group 137B. Lower surface: Green Group 138B. Mature leaves: Upper surface: Green Group 137B. Lower surface: Green Group 137C.
*Petiole.*—Length: 8.9–14.9 cm. Diameter: 0.25 cm. Color: Yellow-Green Group 144A.
*Veins.*—Venation type: Palmate. Color: Upper surface: Yellow-Green Group 144A. Lower surface: Yellow-Green Group 145B.

INFLORESCENCE

Bud:
*Stage of development when bud characteristics determined.*—Bud shows color at side but sepals are not parting at the tips.
*Shape of cluster.*—Elliptical.
*Diameter of cluster.*—1.6–2.2 cm.
*Number of buds per cluster.*—11–16.
*Shape of individual bud.*—Ellipse.
*Length of individual bud.*—0.8–0.9 cm.
*Width of individual bud.*—0.5–0.6 cm.
Natural flowering season at specified location(s): Year round horticultural greenhouse crop.
Blooming habit: Continuous and free flowering.
Umbel diameter: 8.3–10.4 cm.
Umbel depth: 5.5–7.3 cm.
Borne: Umbel, flowers on pedicel, pedicel on peduncle.
Inflorescence position: Above foliage.
Number of inflorescencs per lateral branch: 1–2.
Lastingness of an individual flower: 10–14 days.
Florets:
*Form.*—Flat and slightly cupped. As flowers mature, the florets gradually become more open/flat.
*Number per umbel.*—25–30.
*Diameter.*—4.5 cm.
*Depth.*—1.5 cm.
Petals:
*Color.*—The top two petals have an orange eye whereas the bottoms do not. Upper surface: The top petals are a Red-Purple Group 66A. The bottom ⅓ of the petal has a bright eye of Red Group 43B. The point of connection then immediately fades to White Group 155D. The venation is Red-Purple Group 72B. The bottom petals are solid Red-Purple Group 74A with the point of connection being White Group 155D. The venation is Red-Purple Group 72B. Lower surface: The top two petals are iridescent Red-Purple Group 66B. The bright Red Group 43B eye is also present on the lower side. The connection point is White Group 155D. The venation is Red-Purple Group 71C. The bottom petals are Red-Purple Group 66B fading from the center to the point of connection to White Group 155D. The venation is Red-Purple Group 71B.
*Shape.*—Inverted teardrop.
*Length.*—2.5 cm.
*Width.*—2.7 cm.
*Apex shape.*—Smooth and rounded.
*Base shape.*—Tapered to a point.
*Margin.*—Entire; smooth.
*Number per floret.*—6–8.
*Texture.*—Smooth.
*Tonality from a distance.*—Deep violet-red flowers with fluorescent orange eyes atop of mounding medium-dark green foliage.
Petaloids:
*Quantity.*—0–3 per floret.
*Shape.*—Splits in a two-pronged unit or are tubular.
*Color (upper and lower surface).*—Upper surface is Red-Purple Group 66A and fades to White Group 155D at the point of connection. The lower surface is Red-Purple Group 61C with a hint of Red Group 41B near the base of the petaloid after which it fades to White Group 155D.
*Length.*—1.1–2.1 cm.
*Width.*—0.4–1.4 cm.
Pedicel:
*Length.*—2.5–2.9 cm.
*Diameter.*—0.15–0.2 cm.
*Color.*—Greyed-Purple Group 184D where the pedicel connects to the floret and fades to Yellow-Green Group 144A as the pedicel approaches the point where it connects to the peduncle.
Peduncle:
*Length.*—7.0–15.2 cm.
*Diameter.*—0.25–0.4 cm.
*Texture.*—A slightly rough leather texture with a moderate amount of long pubescence.
*Color.*—Yellow-Green Group 144A.
Sepal:
*Number.*—5.
*Pubescence.*—Moderate.
*Shape.*—Lanceolate.
*Width.*—0.20–0.4 cm.
*Length.*—1.0–1.1 cm.
Fragrance: No unusual fragrance.
Disease resistance: None observed.
Temperature tolerance: None observed.
Drought tolerance: None observed.

REPRODUCTIVE ORGANS

Stamens:
*Number (per flower).*—6–8.
*Filament.*—Length: 0.6–0.8 cm. Color: White Group 155D with the tip being Red-Purple Group 66A.
*Anthers.*—Shape: Oval-like with a slight curve. Length: 0.15–0.2 cm. Color: Greyed-Red Group 182B.
*Pollen.*—Color: Greyed-Orange Group 168B. Amount (generally): Plentiful.
Pistils:
*Number.*—1.
*Length.*—0.9 cm.
*Style.*—Length: 0.3 cm. Color: Red Group 47A.
*Stigma.*—Shape: Style splits and radiates into 5 parts. Color: Red Group 47A. Size: 0.15 cm. high.
*Ovaries.*—Position: Superior. Pubescence: Present. Length: 0.45 cm. Width: 0.15–0.2 cm. Color: Yellow-Green Group 144A.

I claim:

1. A new and distinct variety of *geranium* plant named 'Patriot Bright Violet' as described and illustrated.

* * * * *

UNITED STATES PATENT AND TRADEMARK OFFICE

CERTIFICATE OF CORRECTION

PATENT NO. : PP 17,079 P2
APPLICATION NO. : 11/177056
DATED : September 5, 2006
INVENTOR(S) : Lemon It is certified that error appears in the above-identified patent and that said Letters Patent is hereby corrected as shown below:

Column 4, Line 24, under Pedicel:,
"Color.–Greyed-Purple Group 184D" should read
-- Color.–Greyed-Purple Group 184B --

Signed and Sealed this

Nineteenth Day of December, 2006

JON W. DUDAS
*Director of the United States Patent and Trademark Office*